United States Patent [19]

Marwil

[11] 4,437,941
[45] Mar. 20, 1984

[54] SEPARATION OF HYDROCARBON AND ALCOHOL AZEOTROPIC MIXTURES BY DISTILLATION WITH ANHYDROUS AMMONIA

[75] Inventor: Stanley J. Marwil, Bartlesville, Okla.

[73] Assignee: Phillips Petroleum Company, Bartlesville, Okla.

[21] Appl. No.: 376,075

[22] Filed: May 7, 1982

[51] Int. Cl.³ .......................... B01D 3/36; C07C 7/06; C07C 29/82
[52] U.S. Cl. ...................................... 203/50; 203/19; 203/91; 203/DIG. 13; 568/913; 585/861
[58] Field of Search .................... 203/50, 29, 49, 91, 203/19, DIG. 13; 568/918, 913, 916; 585/861

[56] References Cited

U.S. PATENT DOCUMENTS

| | | | |
|---|---|---|---|
| 1,079,004 | 11/1913 | Golodetz | 203/50 |
| 1,866,800 | 7/1932 | Deanesly | 585/861 |
| 2,822,409 | 2/1958 | Gwynn | 568/913 |
| 2,848,503 | 8/1958 | Fenske | 568/918 |
| 3,732,150 | 5/1973 | Bailey | 203/50 |
| 3,880,929 | 4/1975 | Drake | 564/491 |
| 3,962,337 | 6/1976 | Drake | 564/491 |
| 4,001,294 | 1/1977 | Drake | 260/465.8 R |
| 4,130,484 | 12/1978 | Marwil | 210/689 |
| 4,201,632 | 5/1980 | Martha | 203/51 |

OTHER PUBLICATIONS

Benedict, M. et al., *Extractive and Azeotropic Distillation* Transactions of AICHE, pp. 353-370, Jun. 25, 1945.
Gerster, J. A., *Azeotropic and Extractive Distillation* CEP (vol. 65, No. 9) pp. 43-46, Sep. 1969.
Perry et al., Technique of Organic Chemistry vol. IV—Distillation Interscience Publ., 1965, pp. 423-426 and 457.

*Primary Examiner*—Wilbur L. Bascomb, Jr.

[57] ABSTRACT

A hydrocarbon is removed from an azeotropic mixture of a hydrocarbon and an alcohol by distillation with anhydrous ammonia.

15 Claims, 1 Drawing Figure

SEPARATION OF HYDROCARBON AND ALCOHOL AZEOTROPIC MIXTURES BY DISTILLATION WITH ANHYDROUS AMMONIA

BACKGROUND OF THE INVENTION

This invention relates to the separation of liquid mixtures. It further relates to the separation of hydrocarbon-alcohol azeotropes using anhydrous ammonia as the entraining agent. In one embodiment, it relates to the distillation of cyclohexane from an azeotropic mixture of cyclohexane and t-butyl alcohol.

In certain industrial chemical processes, liquid azeotropic mixtures of a hydrocarbon and an alcohol are used as solvent mediums or are obtained as a byproduct. Such mixtures may be the preferred solvents because of physical or chemical properties of the azeotropic mixture which are not characteristic of the individual components. For example, in the process for preparing mixed, isomeric unsaturated dinitriles from the reaction of acrylonitrile and isobutylene, a step in the production of fiber-grade polyamides, an azeotropic mixture of cyclohexane and t-butyl alcohol is the preferred reaction solvent because it is a stable composition at the reaction conditions and because the mixture has a much lower freezing point than either of its components, each of which freezes above 32° F. and is thus an impractical solvent for a plant process. It has been found that this azeotropic mixture is particularly difficult to separate into its components because the mixture forms solid solutions, making it impossible to separate by crystallization as well as by distillation.

It is thus an object of this invention to provide a method for separating azeotropic mixtures of a hydrocarbon and an alcohol. It is a further object to provide a method for the distillation of cyclohexane from an azeotropic mixture of cyclohexane and t-butyl alcohol.

SUMMARY OF THE INVENTION

According to the invention, azeotropic mixtures comprising a hydrocarbon and an alcohol are separated by distillation using anhydrous ammonia as an entraining agent. According to one embodiment of the invention, cyclohexane is separated from the azeotropic mixture of cyclohexane and t-butyl alcohol by distillation with anhydrous ammonia. According to another aspect, a hydrocarbon is removed from an azeotropic mixture of a hydrocarbon and ethanol by entrainment with anhydrous ammonia.

DETAILED DESCRIPTION OF THE INVENTION

Figure 1:
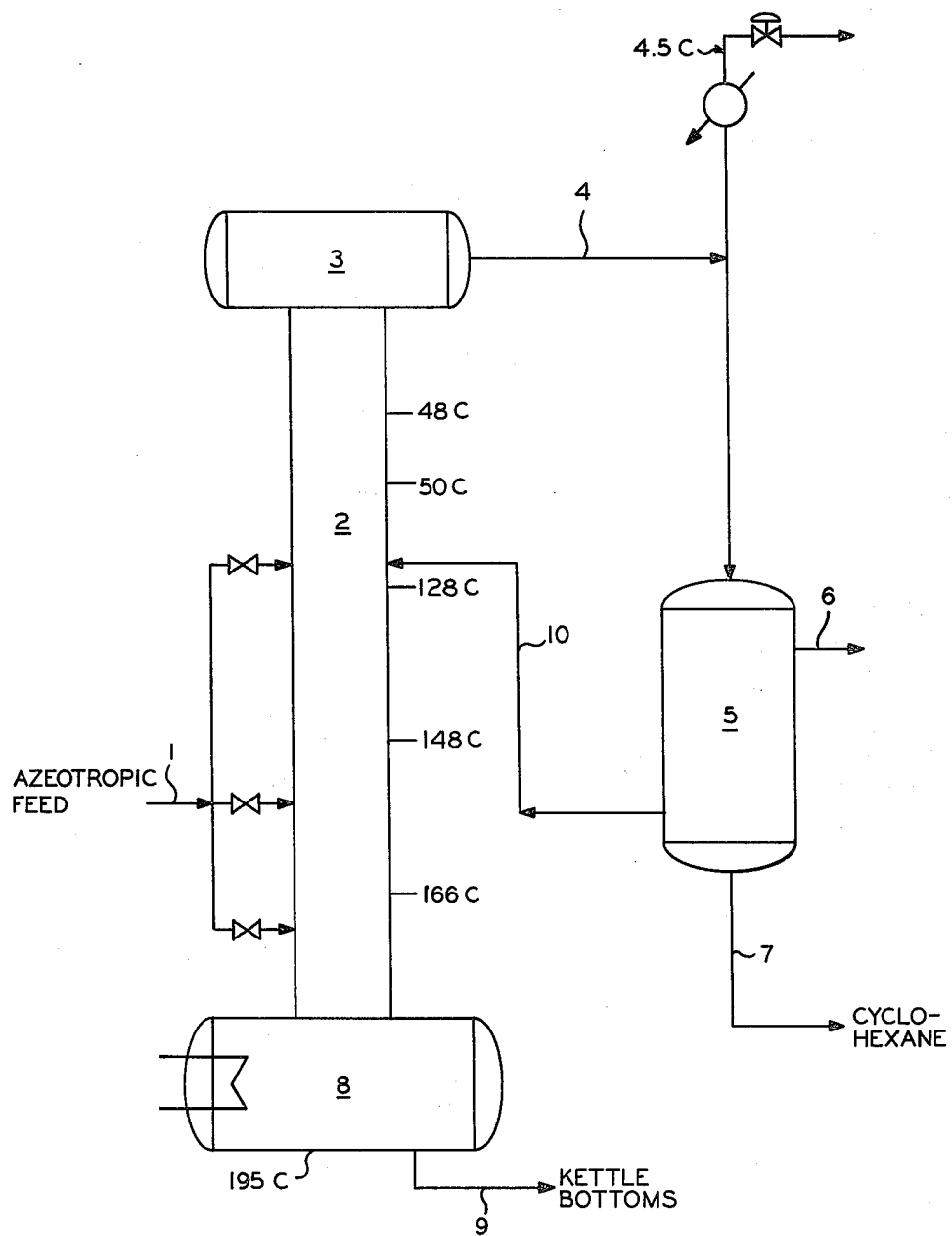

In the invention process for the distillation of an azeotropic mixture of at least one hydrocarbon and at least one alcohol, the mixture is contacted with anhydrous ammonia under suitable distillation conditions, and a mixture of ammonia and at least one hydrocarbon is withdrawn overhead.

Included within the hydrogen-alcohol azeotropic mixtures of the invention process are, for example, the following compositions: t-butyl alcohol and cyclohexane (37:63 weight percent, boiling point 71° C.); t-butyl alcohol and n-heptane (62:38 weight percent, boiling point 78° C); t-butyl alcohol and cyclopentane (7:93 weight percent, boiling point 48.2° C.); n-butyl alcohol and n-octane (50:50 weight percent, boiling point 110.2° C.); isopropyl and benzene (33.3:66.7 weight percent, boiling point 71.9° C.); isopropyl alcohol and cyclohexane (33:67 weight percent, boiling point 68.6° C.); isopropyl alcohol and methycyclopentane (25:75 weight percent, boiling point 63.3° C.); methyl alcohol and n-hexane (26.4:73.6 weight percent, boiling point 50.6° C.); ethyl alcohol and n-hexane (21:79 weight percent, boiling point 58.7° C.); ethyl alcohol and n-heptane (48.2:51:8 weight percent, boiling point 70.9° C.); ethyl alcohol and benzene (32.4:67.6 weight percent, boiling point 68.2° C); isopropyl alcohol and n-hexane (22.6:77.4 weight percent, boiling point 61° C.); isopropyl alcohol and toluene (58:42 weight percent, boiling point 80.6° C.); n-propyl alcohol and benzene (16.9:83.1 weight percent, boiling point 77.1° C.); n-propyl alcohol and toluene (49.5:50.5 weight percent, boiling point 92.6° C.); 1-butyl alcohol and cyclohexane (4:96 weight percent, boiling point 79.8° C.); 1-butyl alcohol and n-heptane (18:82 weight percent, boiling point 93.9° C.).

The separation process can be carried out in a fractionating column, which will in general have at least 15 stages. Generally in such a method, the entraining agent will be introduced in the lower portion of the distillation column as a part of the azeotrope feedstream. The temperature in the lower portion of the distillation column is that which will produce a vapor phase overhead product and a liquid phase bottoms product, the vapor phase comprising the hydrocarbon portion of the azeotrope in combination with the ammonia solvent, and the liquid phase comprising the alcohol component of the azeotrope. The vapor phase may in addition contain a minor amount of the alcohol, and the liquid phase may contain a minor amount of the hydrocarbon. The vapor phase is drawn off overhead, and the liquid phase is removed from the distillation column as a bottoms stream. The ammonia and hydrocarbon can be collected and condensed, producing a liquid mixture which is subsequently separated into a hydrocarbon phase and an ammonia phase. Make-up ammonia solvent can be added to the distillation column as necessary, and the recovered ammonia can be recycled to the azeotrope feed.

The distillation conditions will vary depending upon the system being separated. The weight ratio of the ammonia entraining agent to the feedstream will be broadly from about 1/1 to about 20/1, preferably about 5/1 to 10/1. The head temperature of the distillation column will vary widely depending upon the system being separated, but will generally be below about 55° C. The pressure in the distillation column will generally be about 300 psig.

In one embodiment of the invention, anhydrous ammonia is used as a selective entraining agent for the distillation of cyclohexane from an azeotropic mixture of t-butyl alcohol and cyclohexane. In this process, ammonia and cyclohexane are distilled overhead at an overhead temperature of about 52° to 55° C. Cyclohexane distilled overhead is not soluble in ammonia at ambient conditions. It can be separated from ammonia by cooling and subsequent liquid-liquid phase separation. The distillation tower is preferably operated with a kettle temperature of 195° C., a lower-section temperature of about 148° to 165° C. and an upper section temperature of about 50° C. The pressure in the tower is maintained at about 300 psig.

As shown schematically in the FIGURE, a feed stream 1 containing an azeotropic mixture of about 3.4 weight percent t-butyl alcohol, about 5.7 weight percent cyclohexane and about 90.9 weight percent ammonia is passed into distillation column 2 equipped with internal water condensor 3. The feed is added at a stage in the column maintained at about 150° C. The column is operated at about 300 psig. If the mixture is obtained from a process for the production of 5-methylene-1,9-nonanedintrile, feed stream 1 may also contain MND product from this process. In the distillation column, the mixture is separated into a vaporous cyclohexane phase and a liquid alcohol phase. The cyclohexane plase is condensed in condensor 3 at a temperature of about 45°-50° C. The condensed phase is passed via conduit 4 to phase separator vessel 5, in which liquid-liquid phase separation at ambient temperature and pressure results in a substantially ammonia phase 6 and a substantially cyclohexane phase 7. The bottoms product in kettle 8, maintained at about 195° C., is removed via conduit 9 as a liquid non-azeotropic mixture of t-butyl alcohol, cyclohexane and a minor amount of ammonia. Reflux stream 10 can return a portion of the recovered ammonia to the distillation column.

The process of extractive distillation of cyclohexane from an azeotropic mixture of cyclohexane and t-butyl alcohol has utility in a process for the manufacture of 5-methylene-1,9-nonanedinitrile (MND), a commercially important monomer useful in preparing engineering plastics. MND is prepared by the catalytic hydrogenation of unsaturated aliphatic dinitriles. The process requires an azeotropic mixture of t-butyl alcohol and cyclohexane as a solvent. According to the present invention, anhydrous ammonia can be used as a selective entraining agent for the extractive distillation of cyclohexane from an azeotropic mixture of cyclohexane and t-butyl alcohol used as a solvent in the process of preparing MND.

In another aspect, the invention involves the separation of ethanol from an azeotropic mixture of a hydrocarbon and ethanol. Such a separation process would be useful, for example, in the recovery of ethanol from a biomass fermentation product (ethanol drying). A hydrocarbon which forms an azeotrope with ethanol could be used to separate ethanol from biomass, or an aqueous fermentation broth. The hydrocarbon-ethanol would then be passed through a distillation column to recover the hydrocarbon the recycle and to produce high-quality ethanol product. The ammonia would be used on internal recycle in the distillation column. Hydrocarbons useful in such a process include, for example, hexane, heptane and benzene.

The process of the invention is illustrated by the following examples, in which ammonia is used to entrain a hydrocarbon from an azeotropic mixture of the hydrocarbon and an alcohol.

EXAMPLE I

A liquid mixture containing 63 parts by weight cyclohexane, 37 parts by weight t-butyl alcohol, and 100 parts by weight anhydrous ammonia was fed to a distillation column. The experimental distillation column used for this run was 3 inches in diameter and 12 feet tall. The column was operated at a pressure of about 300 psig at a reflux ratio of 2/1 to 10/1. The extractive distillation tower had 28 stages. The kettle was operated at a temperature of 195° C., the lower section was maintained at a temperature of about 148° to 165° C., and the upper section was about 50° C.

The azeotropic mixture and ammonia were fed as a liquid into the lower portion of the distillation tower at a rate of about 3.52 lb/hr at a temperature of about 150° C. Cyclohexane and ammonia were flashed off overhead, passed to a water cooler and condensed, and passed into a phase separator maintained at ambient temperature and pressure. The upper phase contained about 9.52 weight percent cyclohexane, 0.96 weight percent t-butyl alcohol and 89.52 weight percent ammonia, as determined by gas chromatograph. About 3.15 lb/hr of the solvent phase was recycled to the distillation tower.

In the phase separator an ammonia phase and a cyclohexane phase separated with the ammonia phase containing about 99 weight percent ammonia and about 1 weight percent t-butyl alcohol. The cyclohexane phase contained about 99.5 weight percent cyclohexane and about 0.5 weight percent t-butyl alcohol. The bottoms from the distillation tower were removed as a liquid containing about 18 percent by weight cyclohexane, 2 percent by weight ammonia and the remainder t-butyl alcohol. Thus, the described continuous process was successful in recovering about 90 weight percent of the feed cyclohexane in the azeotropic mixture in an essentially pure stream from the separator.

EXAMPLE II

An azeotropic mixture of n-hexane and ethanol was separated by batch extractive distillation with no external reflux using ammonia as the entraining agent. A mixture of 35.1 weight percent n-hexane, 9.4 weight percent ethanol and 55.5 weight percent ammonia was fed to a distillation column 1 inch in diameter and 10 feet tall. The column was packed with ⅛-inch Fenske packing. Operating conditions were 250 psig and 2.5/1 reflux ratio.

The feed mixture was fed as a liquid into the lower portion of the distillation tower at a temperature of about 45° C. n-Hexane and ammonia were taken off overhead, passed to a water cooler and condensed, and passed into a phase separator maintained at ambient temperature and pressure.

The total overhead contained about 33.9 wt. % n-hexane, 0 wt. % ethanol and 66.1 wt. % $NH_3$.

In the phase separator an ammonia phase and a n-hexane phase separated with the ammonia phase containing about 69.5 wt. % ammonia and 30.5 wt. % n-hexane. The n-hexane phase contained about 99 wt. % n-hexane and about 0 wt. % ethanol and 1% ammonia. The bottoms from the distillation tower were removed as a liquid containing about 35.3 wt. % n-hexane, 53.6 wt. % ammonia and remainder ethanol. The described process recovered only 2 wt. % of the feed n-hexane in the azeotropic mixture in an essentially pure stream from the separator. This small percentage recovery of n-hexane is achieved by batch distillation. It is believed that 80-85 wt. % of n-hexane could be separated out from the azeotropic mixture of n-hexane and ethanol under a continuous distillation operation.

I claim:

1. A process for separating an azeotropic mixture comprising a hydrocarbon and an alcohol which comprises:
    adding to the azeotropic mixture an effective amount of anhydrous ammonia and, under distillation conditions, removing a vapor phase comprising the hydrocarbon, ammonia and no more than a minor amount of the alcohol, and removing a liquid phase comprising the major portion of the alcohol.

2. The process of claim 1 in which the distillation conditions include above-ambient temperature and pressure.

3. The process of claim 1 in which the hydrocarbon is a cyclic hydrocarbon.

4. The process of claim 1 in which the hydrocarbon is an aromatic hydrocarbon.

5. The process of claim 1 in which the hydrocarbon is a $C_1$-$C_{10}$ aliphatic hydrocarbon.

6. The process of claim 1 in which the alcohol is a $C_1$-$C_{10}$ alkanol.

7. The process of claim 6 in which the alkanol is selected from methanol, ethanol, propanol and butanol.

8. The process of claim 1 in which the azeotropic mixture consists essentially of cyclohexane and t-butyl alcohol.

9. The process of claim 8 in which the distillation conditions include a temperature of about 195° C. and a pressure of about 300 psig.

10. The process of claim 1 which further comprises the steps of condensing the vapor phase and separating the resulting liquid into a hydrocarbon phase containing no more than a minor amount of ammonia and an ammonia phase containing no more than a minor amount of hydrocarbon.

11. The process of claim 1 in which the hydrocarbon is n-hexane and the alcohol is ethanol.

12. The process of claim 1 in which the azeotropic mixture is a reaction solvent for the preparation of unsaturated dinitriles.

13. The process of claim 1 in which the ammonia, cyclohexane and minor amount of alcohol are distilled overhead at an overhead temperature of about 52° C. to 55° C.

14. The process of claim 1 in which the weight ratio of the ammonia to the azeotropic mixture is about 1:1 to about 20:1.

15. The process of claim 14 in which the weight ratio of ammonia to the azeotropic mixture is about 5:1 to about 10:1.

* * * * *